United States Patent
Pan et al.

(10) Patent No.: US 9,795,152 B2
(45) Date of Patent: Oct. 24, 2017

(54) 1,3-SPECIFIC INTRAESTERIFICATION

(71) Applicant: Advanta International BV, Amsterdam (NL)

(72) Inventors: Lucas Guillermo Pan, Mar del Plata (AR); Eduardo Pedro Dubinsky, Buenos Aires (AR); Martin Oscar Grondona, Mar del Plata (AR); Andrés Daniel Zambelli, Mar del Plata (AR); Alberto Javier Leon, Mar del Plata (AR)

(73) Assignee: Advanta Holdings BV, Rotterdam (NL)

( * ) Notice: Subject to any disclaimer, the term of this patent is extended or adjusted under 35 U.S.C. 154(b) by 271 days.

(21) Appl. No.: 14/415,122

(22) PCT Filed: Jul. 22, 2013

(86) PCT No.: PCT/EP2013/065419
§ 371 (c)(1),
(2) Date: Jan. 15, 2015

(87) PCT Pub. No.: WO2014/016250
PCT Pub. Date: Jan. 30, 2014

(65) Prior Publication Data
US 2015/0164101 A1 Jun. 18, 2015

(30) Foreign Application Priority Data
Jul. 24, 2012 (WO) ................ PCT/EP2012/064547

(51) Int. Cl.
*A23D 9/00* (2006.01)
*A23D 9/04* (2006.01)
(Continued)

(52) U.S. Cl.
CPC ............... *A23D 9/04* (2013.01); *A23D 7/003* (2013.01); *A23D 7/04* (2013.01); *C11C 3/10* (2013.01); *C12P 7/6454* (2013.01)

(58) Field of Classification Search
CPC ..... C12P 7/64; C12P 7/58; A23D 7/00; A23D 9/00
(Continued)

(56) References Cited

U.S. PATENT DOCUMENTS

| | | | |
|---|---|---|---|
| 5,288,619 A * | 2/1994 | Brown | A23D 9/00 426/33 |
| 6,022,577 A | 2/2000 | Chrysam et al. | |
| 2002/0018841 A1 | 2/2002 | Bons et al. | |

FOREIGN PATENT DOCUMENTS

| | | |
|---|---|---|
| EP | 1689222 B1 | 3/2010 |
| EP | 2204097 A1 | 7/2010 |

(Continued)

OTHER PUBLICATIONS

Brown et al. "Discussion on dietary fat", Journal of Clinical Lipidology, vol. 3, No. 5, 2009, pp. 303-314.
Guerri et al. "Studies on transesterification. IV. Transesterification experiments direct towards S2U triglycerides", Database FSTA (Online), International Food Information Service (IFIS), Frankfurt-Main, Germany, 1972, 1 page. (Abstract only).
(Continued)

*Primary Examiner* — Helen F Heggestad
(74) *Attorney, Agent, or Firm* — Rudy J. Ng; Bret E. Field; Bozicevic, Field & Francis LLP (57) ABSTRACT

The present invention relates to a method for increasing the SUS content in an oil or in an olein fraction, comprising performing 1,3-selective enzymatic intraesterification on a natural starting oil or olein fraction prepared therefrom wherein the ratio between SUS and SUU is at least 1:1.5 and the SSS content is low, in particular close to 0%. Further, the present invention relates to 1,3-Selective intraesterified oil or olein, obtainable by performing the present method.

33 Claims, 5 Drawing Sheets

(51) Int. Cl.
    A23D 7/00    (2006.01)
    C11C 3/10    (2006.01)
    A23D 7/04    (2006.01)
    C12P 7/64    (2006.01)

(58) Field of Classification Search
    USPC .................................. 426/33, 601, 607, 603
    See application file for complete search history.

(56) References Cited

FOREIGN PATENT DOCUMENTS

| JP | H06-240290 A | 8/1994 |
| JP | 2001-321076 A | 11/2001 |
| JP | 2009-543907 A | 12/2009 |
| RU | 2445351 C2 | 3/2012 |
| WO | 2011037296 A1 | 3/2011 |

OTHER PUBLICATIONS

Silva et al. "The effects of enzymatic interesterification on the physical-chemical properties of blends of lard and soybean oil", LWT—Food Science and Technology, vol. 42, No. 7, 2009, pp. 1275-1282.

Svensson et al. "Effect of acyl migration in Lipozyme TL IM-catalyzed interesterification using a triacylglycerol model system", European Journal of Lipid Science and Technology, vol. 113, 2011, pp. 1258-1265.

Lin et al., High oleic enhancement of palm olein via enzymatic interesterification, J Oleo Sci. 2009;58(11):549-55.

Gunstone, Vegetable Oils in Food Technology: Compositions, Properties, and Uses, Second Edition, Chapter 2, Palm Oil, p. 26-31, Published by Blackwell Publishing Ltd. 2011.

\* cited by examiner

$$[XYZ]_F = (2 - 1_{\{X=Z\}}) \frac{[X_{1,3}^*][Y_2][Z_{1,3}^*]}{(2T_0 + S_0)^2}, \text{ where}$$

$$[X_{1,3}^*] = \sum_{Y,Z}[XYZ]_0 + \sum_{W,Y}[WYX]_0 + 1_{\{X=S\}}S_0 ;$$

$$[Z_{1,3}^*] = \sum_{X,Y}[XYZ]_0 + \sum_{Y,W}[ZYW]_0 + 1_{\{Z=S\}}S_0 ;$$

$$[Y_2] = \sum_{X,Z}[XYZ]_0$$

$1_{\{W=S\}}$ is an indicator function that takes the value " 1" if W=S, and "0" otherwise.

There are several assumptions for these calculations to be true, among them, the enzyme has 1,3-positional specificity and has no fatty acid specificity, there are no losses of enzyme activity during the course of the reaction, steady state is achieve after some time, there is no formation of diglycerides, no trans-insteresterification and the total moles of the oil at any time, $[T]_t = T_0$, similarly, $[P]_t + [S]_t + [O]_t + [L]_t + [A]_t + [B]_t = S_0$.

| Sample | Melting points (°C) |
|---|---|
| HSHO | 14.3 |
| HSHO olein | 14.1 |
| HSHO RMIM | 20.8 |
| HSHO TLIM | 26.4 |
| Olein RMIM | 19.6 |
| Olein TLIM | 23.6 |

1,3-SPECIFIC INTRAESTERIFICATION

The present invention relates to a process for altering the triacylglyceride (TAG) content of an oil or oil fraction, in particular an olein fraction.

Some food products, such as margarine, spreads, coatings, fillings, frying oils and cooking oils, require specific properties such as spreadability, firmness, plasticity, mouth feel and the release of flavour. Natural vegetable fats or oils used for food products often do not have these properties and require modification before they can be used. The main processes used for modification of fats or oils are fractionation, hydrogenation, and interesterification. These processes are known in the art and are, for instance, described in "Food Fats and Oils", Ninth Edition; Institute of Shortening and Edible Oils.

Fractionation is the process in which the liquid and solid constituents of a fat or oil are separated and relies on the differences in melting points. For example, fractionation of a high stearic high oleic oil results in a solid, the stearin, fraction and a liquid, the olein, fraction.

Hydrogenation is a chemical reaction commonly used to convert unsaturated fatty acids to saturated fatty acids. Apart from converting liquid oils to semi-solids and/or solids, hydrogenation also increases the oxidative and thermal stability of the fat or oil. Hydrogenation can be partial or complete. Partial hydrogenation results in oils and fats of different melting ranges that depends on the hydrogenation degree and process conditions and is often used in the production of cooking oils and margarines. A major disadvantage of partial hydrogenation is that it results in high levels of trans-isomers which have been implicated in cardiovascular disease.

In interesterification two or more desired oils are blended and the fatty acids of these oils are redistributed between the triglycerides. The selection and proportions of the fat or oil types that go into the reaction mixture determine the properties of the resulting fat or oil. Interesterification can be performed by chemical or enzymatic processes. In chemical interesterification two or more desired oils are blended, dried and a catalyst such as sodium methoxide is added. This process results in the random distribution of the fatty acids across the glycerol backbones of the triglycerides. Enzymatic interesterification involves the random or position-specific redistribution of fatty acids by using an enzyme.

The present inventors have now found that the enzymatic redistribution of fatty acids can be performed with only one fat or oil type instead of two or more fat types. The process in which only one fat or oil type is used is referred to herein as "1,3-selective enzymatic intraesterification". This process can be applied but not exclusively, to relatively new modified oils like high stearic high oleic oils, more in particular HSHO sunflower oil, in which a significant amount of saturated-unsaturated-unsaturated (SUU) type triglycerides is present to increase the content of SUS type triglycerides. These types of oil have a TAG distribution that allows the internal fatty acid rearrangement of the invention that leads to an enrichment of the oil or olein in SUS type triglycerides.

It is thus the object of the present invention to increase the SUS content in an oil or olein fraction. It is a further object of the invention to increase the yield of stearin upon fractionation of oils and oleins. In the research that led to the present invention, it was found that the SUS content of fats and oils can be increased by the process of 1,3-selective intraesterification. With this process it is now possible to increase the amount of saturated-unsaturated-saturated (SUS) type triglycerides in one fat type or oil which is normally rich in saturated-unsaturated-unsaturated (SUU) type triglycerides. Hereby, the functional properties of the one fat type or oil can be improved for food applications, such as, but not limited to, margarines, spreads, coatings, filings, and cooking oils.

The invention thus relates to a method for increasing the SUS content in an oil or in an olein fraction while the SSS content is kept low, comprising performing 1,3-selective enzymatic intraesterification on a natural starting oil or olein fraction prepared therefrom wherein the ratio between SUS and SUU is at least 1:1.5 and the SSS content is low, in particular close to 0%.

The natural starting oil is a single oil extracted from an oil source and not blended with other oils. According to the invention it is now possible to effect the rearrangement of fatty acids within an oil so that the content of SUS type TAGs is increased in the end-product of the intraesterification.

The ratio between SUS and SUU is at least 1:1.5 in order for the method to work properly. This is because the conversion from SUU to SUS is an equilibrium reaction. Only with a SUU that is higher than the content of SUS a significant increase in SUS content can be obtained. A significant increase is an increase of at least 2%, preferably at least 3%, more preferably at least 5% but is most preferably at least 12%. The ratio between SUS and SUU (SUS:SUU) in the starting oil or olein fraction is therefore in order of increased preference at least 1:1.5, at least 1:2, at least 1:3.5, at least 1:5, at least 1:7.5, at least 1:10, at least 1:15.

The inventors have found that the method of the present invention works best when the starting oil or starting olein fraction has a SUU content of 30% or higher, preferably a SUU content of 35% or higher, more preferably a SUU content of 40% or higher, even more preferably a SUU content of 50% or higher.

In a preferred embodiment of the present invention, the starting oil or starting olein fraction has a minimum SUU content of 40% and a maximum SUS content of 5%, a minimum SUU content of 40% and a maximum SUS content of 10%, a minimum SUU content of 50% and a maximum SUS content of 10%, or a minimum SUU content of 50% and a maximum SUS content of 40%.

The method of the invention can be performed with different oils and oleins obtained from an oil source that is high in stearic or palmitic acid. Examples of such oil sources are high stearic high oleic sunflower seed, high stearic high oleic soybean, high stearic high oleic cottonseed, shea fruits, high stearic high oleic rapeseed.

The starting oil or olein fraction is preferably selected from high stearic high oleic (HSHO) sunflower oil, high stearic high oleic soybean oil, high stearic high oleic cottonseed oil, shea olein, palm superolein or top olein or high stearic high oleic rapeseed oil. The main characteristic in these types of oil is that U (unsaturate fatty acid) is essentially O (oleic acid). This characteristic differentiates this type of oils from regular oils in which the main U is L (linoleic).

The differences between both types of SUS Triglycerides are melting behavior and oxidative stability. SOS type (saturate-Oleic-saturate) has melting points above 34° C. This fact conferes them very special characteristics depending on their relative concentration in the matrix (commercial fats and oils) in which they are present. When the concentration is high (about 80%), as in cocoa butter, the fat is brittle at room temperature and melts completely in the mouth (body temperature), which are the highly appreciated characteristics of chocolate and cocoa butter alternatives. When the concentration is still significant (about 35%), they can be used as structuring fats i.e. in margatines and spreads. This means the capacity of retaining very high amounts of liquid oils in a special crystal network, that conferes these kind of products the spreadability at low temperatures (when taking from the fridge) and a melting stability at room temperature by retaining the liquid oil. This doesn't happen with SLS type of triglycerides.

Another important characteristic is the oxidative stability. This is because the oxidation rate of linoleic acid (the main one in most of the liquid regular seedoils) is 40 times faster than oleic acid. This means that triglycerides in which U (unsaturated fatty acid) is L (linoleic acid) and accordingly the commercial fats with this kind of triglycerides, has a lower shelf life (or rancidity resistance) than those in which U is O (oleic acid).

A third significant point is when S (saturate fatty acid) is stearic acid and U is oleic acid. (this is valid for high stearic high oleic oils and fractions but not for palm oleins in which the main S is palmitic acid). Stearic acid is the only saturated fatty acid with the ability of generating solid or semisolid fats that is not considered harmful from a nutritional point of view because it has a neutral behavior regarding LDL cholesterol ("bad cholesterol"). On the other hand a high concentration of oleic acid (a stable unsaturated) has a positive effect in lowering LDL cholesterol. In that way the HSHO oils (high stearic high oleic oils) and oleins, are a good alternative to trans fats and other saturates (like palm oil and fractions), that increases de LDL cholesterol and the CVD (cardiovascular disease) risk.

Further the high stearic high oleic oils and fractions preferably used in the present invention (coming from modified traditional crops like sunflower, rapeseed, soybean, cottonseed) being originated from annual crops are more sustainable than tropical fats, specially because of the clearing of rainforest that takes place in the main palm oil producing countries, with very deleterious effect on environment.

According to a further aspect thereof the method described above can be used in a method for increasing the stearin yield from a starting oil or starting olein fraction upon fractionation thereof. A predictive model was developed combining fractionation and 1,3 enzymatic intraesterification process This method comprises the steps of:

a) optionally fractionating a starting oil having a ratio between SUS and SUU of at least 1:2 and a low SSS content, in particular close to 0%, to obtain a $1^{st}$ stearin fraction and a starting olein fraction;

b) performing 1,3-selective enzymatic intraesterification on a natural starting oil or olein fraction prepared therefrom wherein the ratio between SUS and SUU is at least 1:1.5 and the SSS content is low, in particular close to 0% on the starting oil or starting olein fraction to obtain 1,3-selective intraesterified oil or olein having a higher SUS content than the starting oil or olein fraction;

c) fractionating the 1,3-selective intraesterified oil or olein thus obtained to obtain a $2^{nd}$ stearin fraction and an olein fraction.

This method enables the obtention of an extra stearin fraction from the initial starting oil by performing a further fractionation step after the intraesterification process has taken place on the starting olein The stearin yield in the second fractionation performed after intraesterification of the starting olein is the gain of the overall process. The intraesterification has enriched the olein in SUS and thus allows the obtention of an extra stearin fraction from an olein that was initially exhausted but has gained extra SUS by means of the intraesterification process of the invention.

Thus, the total stearin yield from steps a) and c) above together is higher than the stearin yield after fractionating the starting oil.

In case the method is applied to an oil, there are thus two possible scenario's, one wherein the starting oil is fractionated and one wherein the starting oil is not fractionated before 1,3-selective intraesterificaton takes place. Fractionation of the starting oil results in a stearin fraction and an olein fraction, of which the olein fraction is subsequently subjected to 1,3-selective intraesterification. This results in the production of 1,3-selective olein. However, in case the starting oil is not first fractionated, 1,3-selective intraesterification is performed on the entire oil and the resulting product is 1,3-selective intraesterified oil.

Another scenario is when not an entire oil but an olein fraction is used as the starting material for 1,3-selective intraesterification. In this case, the fractionation of step a) does not takes place within the claimed process and 1,3-selective intraesterification on the olein fraction results in the production of 1,3-selective intraesterified olein obtained by the method of the invention.

The products of these processes, the 1,3-selective intraesterified oil and 1,3-selective intraesterified olein, are subsequently fractionated in order to obtain the stearine fraction and another olein fraction.

The terms "SUS", "SUU" and "SSS" refer to the saturated-unsaturated-saturated (SUS), saturated-unsaturated-unsaturated (SUU), and saturated-saturated-saturated (SSS) types of triglycerides (TAGs), wherein "S" represents a saturated fatty acid and "U" represents an unsaturated fatty acid. Other types of triglycerides include, for instance, unsaturated-unsaturated-unsaturated (UUU), unsaturated-saturated-unsaturated (USU), unsaturated-unsaturated-saturated (UUS), saturated-saturated-unsaturated (SSU), and unsaturated-saturated-saturated (USS). Examples of saturated fatty acids include, but are not limited to, stearic acid and palmitic acid. Examples of unsaturated fatty acids include, but are not limited to, palmitoleic acid, oleic acid, and linoleic acid.

In a preferred embodiment of the present invention, the "U" in SUS and/or SUU is oleic acid.

The triglyceride content is expressed herein in percentages of the entire oil. A SUS content of lower than 30% thus means that less than 30% of the total triglycerides of the oil are of the SUS type.

The SSS content in the starting oil or starting olein fraction should be kept as low as possible because SSS confers to the oil a waxy palatability because its high melting point. With the term "low" is meant less than 1%. If the 1,3 intraestrified oil or olein is submitted to a second fractionation, the SSS content should be less than 0.3%. Preferably, the SSS content is 0%, or close to 0%.

1,3-Selective intraesterification can be performed following standard techniques known to a person skilled in the art. However, it should be noted that the 1,3-Selective intraesterification as used herein refers to the process in which fatty acids at positions 1 and 3 of the triglycerides are redistributed between the triglycerides of only one type of oil or olein fraction, i.e. on a single oil extracted from an oil source and not blended with other oils.

The term "fat" as used herein also refers to "oil", and vice versa. These terms also refer to "lipid". The words "oil" and "fat" are used interchangeably herein.

The term "olein fraction" refers to the liquid fraction from an oil obtained by fractionation of the oil. Fats or oils consist of a wide group of compounds that are generally soluble in organic solvents and generally insoluble in water. Chemically, fats are triglycerides, triesters of glycerol and any of several fatty acids. In the context of the present invention the term "fat" or "fats" is intended to refer to a mixture of triglycerides. A triglyceride, also referred to as TG, triacylglycerol, TAG, or triacylglyceride, is an ester derived from glycerol and three fatty acids. The fatty acids can be any and any combination of fatty acid. A fatty acid is a carboxylic acid with a long aliphatic tail (chain), and is either saturated or unsaturated. Fatty acids that have double bonds are known as unsaturated. Unsaturated fats have a lower melting point and are more likely to be liquid. Fatty acids without double bonds are known as saturated. Saturated fats have a higher melting point and are more likely to be solid. As such, fats may be either solid or liquid at room temperature, depending on their structure and composition.

As mentioned above the term "fat" as used herein refers to a mixture of triglycerides. The mixture of triglycerides may comprise one or more types of triglycerides. Types of triglycerides include for instance unsaturated-unsaturated-unsaturated (UUU), saturated-unsaturated-unsaturated (SUU), unsaturated-saturated-unsaturated (USU), unsaturated-unsaturated-saturated (UUS), saturated-saturated-unsaturated (SSU), saturated-unsaturated-saturated (SUS), unsaturated-saturated-saturated (USS), and saturated-saturated-saturated (SSS).

The type of oil or olein fraction can be obtained from any source. Preferably, the oil or olein fraction is obtained from a vegetable source, including, but not limited to, palm, soybean, rapeseed, sunflower seed, peanut, cottonseed, palm kernel, coconut, olive, corn, grape seed, nuts, linseed, rice, safflower, and sesame seeds.

The 1,3-selective intraesterification can be achieved by using different types of enzymes, such as lipases, and include, but are not limited to, RMIM and TLIM.

In a preferred embodiment of the present invention, the 1,3-selective intraesterification is performed by using the RMIM or TLIM enzyme. RMIM is lipase from *Rhizomucor miehei* whereas TLIM is a lipase from *Thermomyces lanuginosis* (TLIM). Both enzymes can be obtained from Novozymes.

Methods for enzymatic redistribution of fatty acids are known in the art and have been described in, for instance, ("Food Fats and Oils", Ninth Edition; Institute of Shortening and Edible Oils).

During 1,3-selective intraesterification, the SUS content is increased by switching SUU type triglycerides into SUS type triglycerides, thereby increasing the solid fat content of the oil or olein fraction. It is also possible to lower an undesirable high solid fat content (SFC) level, for instance, in margarine a high level of SUU type triglycerides yields a high level of solid fat content (SFC) at fridge temperatures (below 10° C.). The consequence of this is a worse spreadability of the margarine. On the other hand a low level of SUS type triglycerides yields a low solid fat content (SFC) level at room temperature. The consequence is that margarine could melt on the table. By applying 1,3-selective intraesterification both issues could be solved.

By increasing the SUS content in an oil or olein fraction, it is possible to obtain more stearin from this oil or olein fraction, which may then be used in several applications, including, but not limited to, use as a structuring fat.

The fractionation step (a) is optional because the 1,3-selective intraesterification may be applied to an entire oil as well as an olein fraction.

The method for increasing the stearin yield from a starting oil or starting olein fraction may further comprise repeating steps (b) and (c) one or more times to obtain further stearin fraction(s) and olein fraction(s). The further stearin fraction(s) thus obtained may be combined with the stearin fraction obtained in step (a) and the further stearin fraction obtained in step (c) to even further increase the total stearin yield obtainable from a single unblended oil.

Fractionation is the process in which the solid and liquid fractions from a fat are separated. Different methods for fractionation are known to a person skilled in the art. These methods include, but are not limited to, winterization, pressing, dry fractionation and solvent fractionation. Dry fractionation can be performed by, for example, crystallization.

A drawback of enzymatic 1,3-selective intraesterification might be that it is not as fast as chemical 1,3-selective intraesterification. As the reaction time increases, the selectivity of the enzymes for positions 1 and 3 of the triglycerides may decrease. As a result, part of the SUU is converted into SSS instead of SUS. It is thus preferred to optimize the reaction time in order to obtain the maximum increase in SUS content and to minimize the SSS content. The SSS content that is still acceptable will depend on the application of the end product.

In a preferred embodiment of the present invention, the reaction time of the 1,3-selective intraesterification when using RMIM or TLIM is at least about 30 minutes, preferably between about 2 and 8 hours, more preferably between about 2 and 6 hours, even more preferably between about 2 and 4 hours, and most preferably about 4 hours.

The optimal reaction time depends on the enzyme that is used. A person skilled in the art would realize that if an enzyme other than RMIM or TLIM is used, the reaction time can be different.

The invention further relates to 1,3-selective intraesterified oil or olein, obtainable by performing the method of the invention. The 1,3-selective intraesterified oil or olein is enriched in SUS as compared to the oil it was produced from.

The present invention will be further illustrated in the examples that follow and that are not intended to limit the invention in any way. In the examples reference is made to the following figures.

FIGURES

FIG. 2 shows the predictive equation obtained for 1,3-selective intraesterification. The equations are developed for a more general interesterification process (selective 1,3 acidolysis). Selective 1,3 intraesterification happens when $S_o=0$. All computations are based on moles. For simplification we will assume that the acid in the interesterefication is stearic S. Let $T_0$ the initial total mole concentration of the oil, $[XYZ]_0$ be the initial total mole concentration of a particular TAG XYZ, where X, Y, Z could be P, S, O, L, A or B, let $S_o$ be the initial total numbers of Stearic moles. The expected final mole concentration $[XYZ]_F$ is given by the expression in FIG. 2. $1_{\{W=S\}}$ is an indicator function that takes the value "1" if $W=S$, and "0" otherwise. There are several assumptions for these calculations to be true, among them, the enzyme has 1,3-positional specificity and has no fatty acid specificity, there are no losses of enzyme activity during the course of the reaction, steady state is achieve after some time, there is no formation of diglycerides, no trans-insteresterification and the total moles of the oil at any time, $[T]_t=T_0$, similarly, $[P]_t+[S]_t+[O]_t+[L]_t+[A]_t+[B]_t=S_0$.

EXAMPLES

Example 1

1,3-Selective Intraesterification of HSHO Sunflower Oil and Olein Fraction

Trials were performed with HSHO oil and a HSHO olein fraction using two different enzymes, RMIM and TLIM (obtained from Novozymes), which are selective for sn-1 and sn-3 positions of the triglycerides. In these trials 100 g of the oil or olein was treated with 10 g of either of the two enzymes at a temperature of 60° C. The reaction time was 4 hours.

Results are shown in Table 1 that shows the TAG composition of the starting oil and the starting olein fraction, and their 1,3-selective intraesterified products. Results are given for two different enzymes.
The SUS content in the intraesterified products of both the HSHO oil and the HSHO olein fraction is significantly increased, while the SUU content is significantly decreased.

TABLE 1

|  | SSS | SUS | SUU | UUU | StOSt | StOO |
|---|---|---|---|---|---|---|
| HSHO (Before ER) | 0.0 | 9.4 | 51.8 | 38.8 | 4.1 | 30.7 |
| ER HSHO oil (enzyme RMIM) | 0.0 | 11.3 | 43.0 | 45.7 | 5.0 | 25.3 |
| ER HSHO oil (enzyme TLIM) | 0.8 | 11.9 | 40.5 | 46.7 | 5.2 | 23.4 |
| HSHO olein (Before ER) | 0.0 | 7.1 | 51.8 | 41.1 | 2.1 | 31.1 |
| ER HSHO olein (enzyme RMIM) | 0.3 | 11.1 | 42.6 | 46.0 | 4.2 | 23.6 |
| ER HSHO olein (enzyme TLIM) | 0.7 | 11.5 | 40.3 | 47.5 | 4.3 | 22.1 |

ER (Enzymatic 1,3 Rearranged)

The SSS content is higher for the TLIM enzyme than for the RMIM enzyme, which means that the RMIM enzyme is more selective than the TLIM enzyme as expected. When using the TLIM enzyme it may be beneficial to further decrease the reaction time in order to minimize the SSS content in the intraesterified product.

Example 2

Method for Increasing the Stearin Yield Upon Fractionating a HSHO Sunflower Oil or Olein Fraction In a first preliminary trial, an HSHO sunflower oil having a SUS content of 9.4 was selected and subjected to a first fractionation step to yield 12.0% stearin and 88.0% olein. In short, the oil was melted and heated up to 60° C. Then, the temperature was decreased gradually until 17/20° C. The oil was then held at this fractionation temperature during 16 hrs. Stearin was separated through a membrane press filter with squeezing pressures up to 6 bars. The resulting stearin fraction had a SUS content of 38.8% which defines the quality of the final product.

Figure 1:
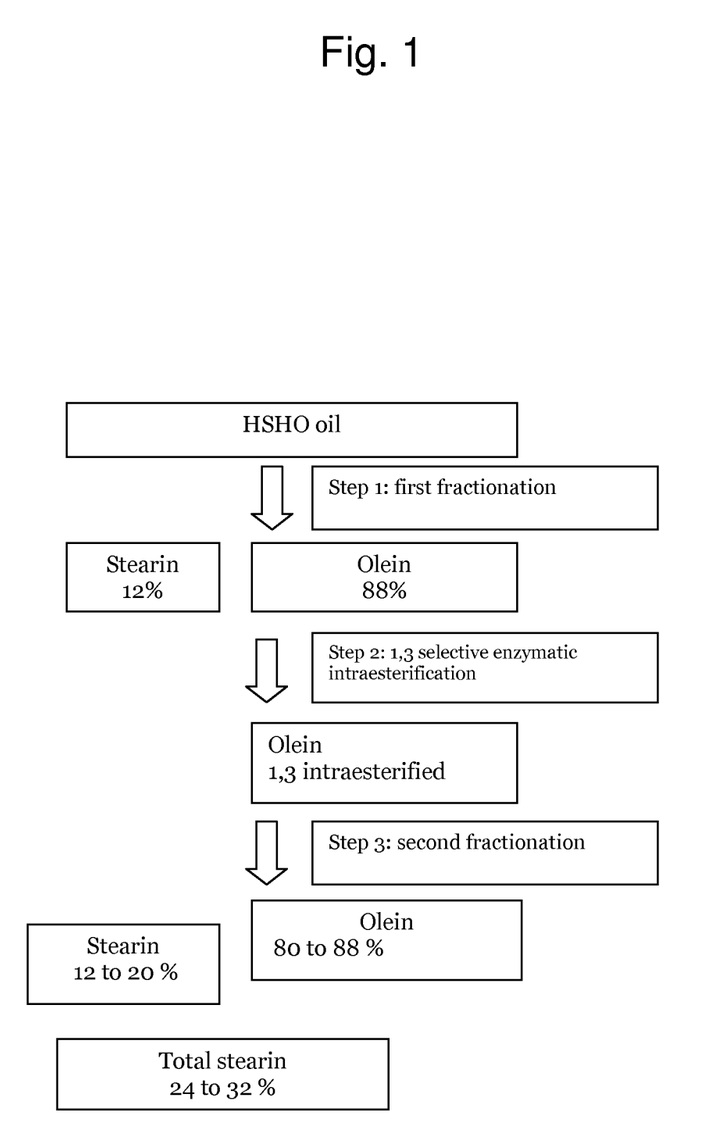
FIG. 1 shows a schematic overview of the method for increasing the stearin yield.
Figure 2:
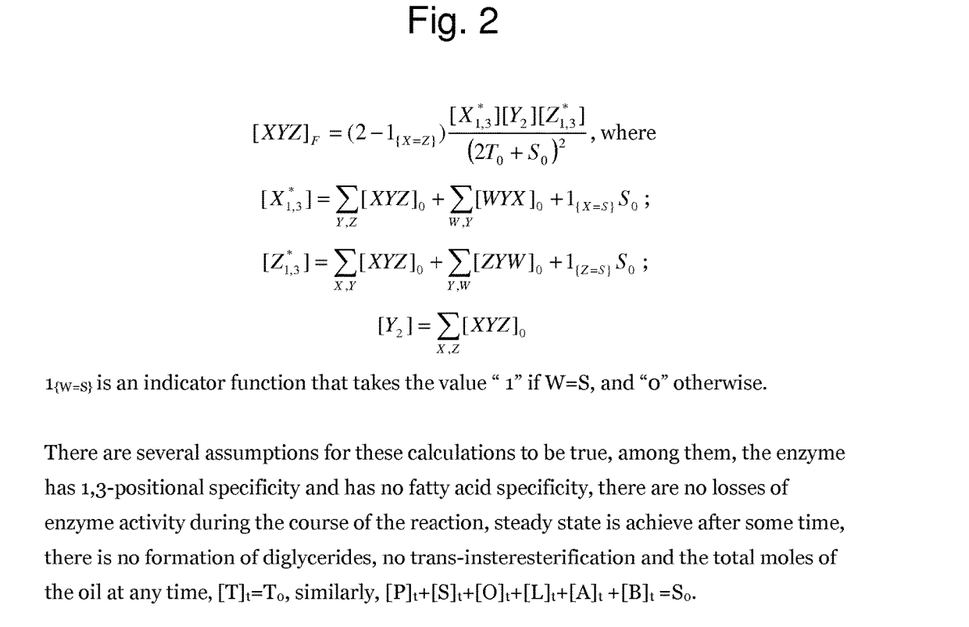

The remaining SUS concentration in the olein fraction was 5.5. This SUS concentration was subsequently increased to 9.0 by 1,3-selective intraesterification. This value was determined by using the predictive equation shown in FIG. 2. The resulting 1,3-selective intraesterified olein was then used in a second fractionation step to again obtain a stearin and olein fraction. According with the level of exhaustion of SUS in the olein in the fractionation steps, yields of stearin in the second fractionation step could range from 12.0% to 20%. Then yields for olein would be 88% and 80%, respectively. This means that the total stearin yield could range from 24 to 32.0%, which is an increase of about 12% to 20% when compared to not performing the 1,3-selective intraesterification step. One can envisage that repeating the 1,3-selective intraesterification and second fractionation steps may even further increase the stearin yield. A schematic overview of this process is shown in FIG. 1.

Example 3

Determination of Reaction Conditions 1,3-Selective intraesterification is accomplished by means of enzymes (lipases). One issue that arises during this process is that with an increase in reaction time, selectivity of the enzyme for the sn-1 and sn-3 positions of the triglycerides may decrease. As a result, the SSS content in the resulting intraesterified oil or olein fraction may be higher than is desired. Therefore, a preliminary trial was performed to determine the optimum reaction time at which the amount of SUS is maximized without significantly increasing the amount of SSS.

Figure 3:
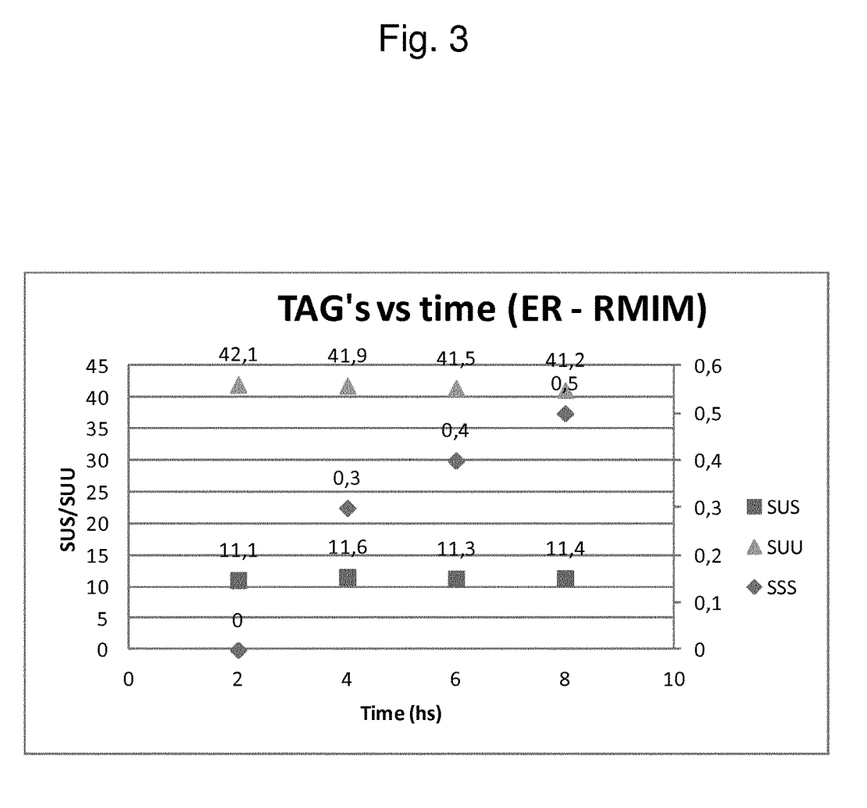
FIG. 3 shows the results of the optimization of the reaction time when using the RMIM enzyme.

High stearic high oleic (HSHO) olein was intraesterified with 10% (w/w) of the Lipozyme RMIM enzyme (obtained from Novozymes). Samples were taken at 2, 4, 6 and 8 hours and analyzed after the separation of the enzyme. The results are shown in FIG. 3.

The reaction time of 4 hours was chosen as the tentative optimum time for further trials.

Example 4

Determination of Solid Fat Content

The solid fat content (SFC) of the HSHO oil, HSHO olein fraction and the 1,3-selective intraesterified products were determined using DSC.

Figure 4:
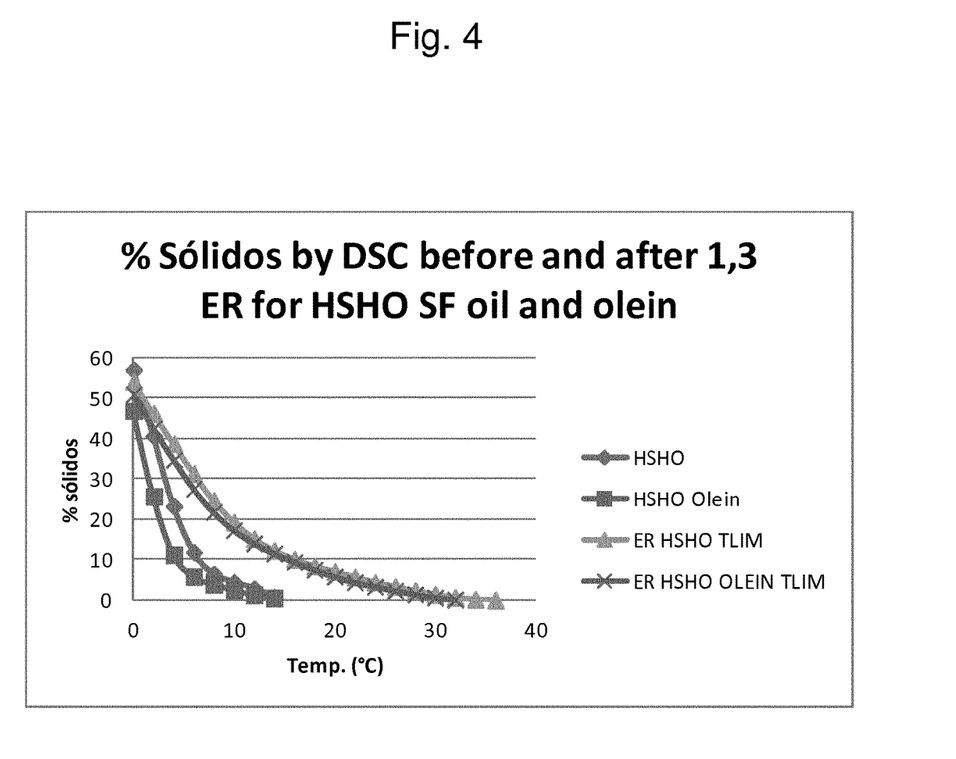
FIG. 4 shows the solid fat content of the starting oil and starting olein fraction, and their 1,3-selective intraesterified products.

FIG. 4 shows that the solid fat content of the 1,3-selective intraesterified products is higher than the solid fat content of the original HSHO oil and HSHO olein fraction at temperatures above 0° C.

Example 5

Determination of Melting Point

The melting point of the HSHO oil, HSHO olein fraction and 1,3-selective intraesterified products was determined using standard techniques.

Figure 5:
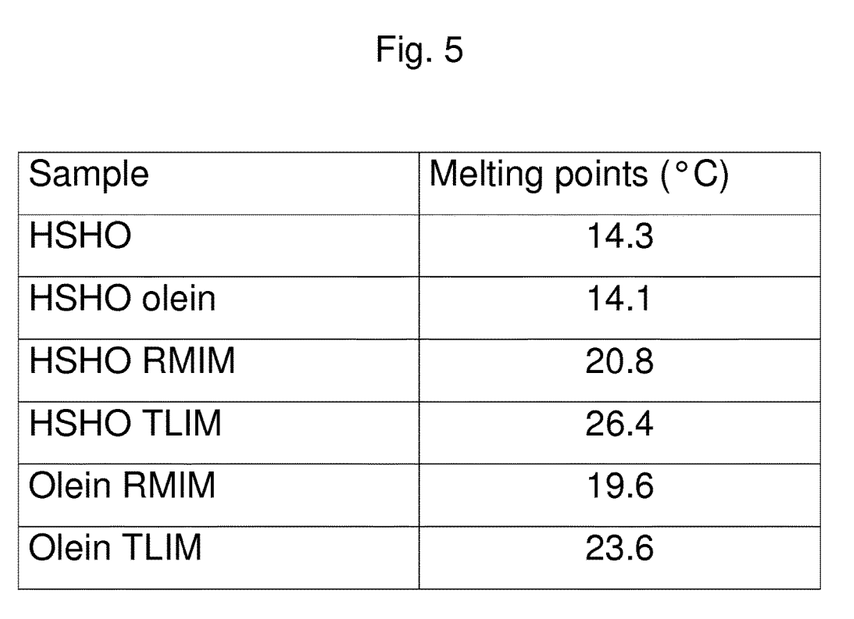
FIG. 5 shows the melting point of the starting oil and starting olein fraction, and their 1,3-selective intraesterified products.

FIG. 5 shows that the melting point of the 1,3-selective intraesterified HSHO oil and HSHO olein fraction are significantly increased when compared to the original HSHO oil and HSHO olein fraction.

The invention claimed is:

1. A method for increasing the SUS content in an oil, comprising performing 1,3-selective enzymatic intraesterification on a natural starting oil wherein the ratio between SUS and SUU is at least 1:1.5 and the SSS content is low.

2. The method as claimed in claim 1, wherein the natural starting oil is a single oil extracted from an oil source and not blended with other oils.

3. The method as claimed in claim 1, wherein the ratio between SUS and SUU is in order of increased preference at least 1:1.5, 1:2, 1:3.5, 1:5, 1:7.5, 1:10, 1:15.

4. The method as claimed in claim 2, wherein the oil source is sunflower seed, soybean, cottonseed, shea fruits, or rapeseed.

5. The method as claimed in claim 1, wherein the starting oil is high stearic high oleic (HSHO) sunflower oil.

6. The method as claimed in claim 1, wherein the starting oil is selected from high stearic high oleic soybean oil, high stearic high oleic cottonseed oil and high stearic high oleic rapeseed (canola) oil.

7. The method as claimed in claim 1, wherein the starting oil is a tropical oil selected from shea olein and palm olein.

8. A method for increasing the stearin yield from a starting oil, comprising the steps of:
   a) performing the method as claimed in claim 1 on the starting oil to obtain 1,3-selective intraesterified oil having a higher SUS content than the starting oil; and
   b) fractionating the 1,3-selective intraesterified oil thus obtained to obtain a stearin fraction and an olein fraction.

9. The method as claimed in claim 1, wherein the unsaturated U in SUS and/or SUU is oleic acid.

10. The method as claimed in claim 1, wherein the reaction time of the 1,3-selective enzymatic intraesterification is at least about 30 minutes.

11. The method as claimed in claim 1, wherein the 1,3-selective enzymatic intraesterification is performed by using lipase enzymes.

12. A composition comprising a 1,3-selective intraesterified oil, obtainable by performing a method as claimed in claim 1, wherein the 1,3-selective intraesterified oil is enriched in SUS as compared to the oil it was produced from.

13. A composition consisting of a stearin fraction, obtainable by performing the method as claimed in claim 8.

14. The composition of claim 13, wherein the composition is selected from the group consisting of a margarine, spreads, coatings, fillings, frying oils and cooking oils.

15. The method as claimed in claim 11, wherein the lipase enzyme comprises a lipase from *Rhizomucor miehei* (RMIM).

16. The method as claimed in claim 11, wherein the lipase enzyme comprises a lipase from *Thermomyces lanuginosis* (TLIM).

17. A method for increasing the SUS content in an olein fraction, comprising performing 1,3-selective enzymatic intraesterification on an olein fraction prepared from a natural starting oil wherein the ratio between SUS and SUU is at least 1:1.5 and the SSS content is low.

18. The method as claimed in claim 17, wherein the natural starting oil is a single oil extracted from an oil source and not blended with other oils.

19. The method as claimed in claim 17, wherein the ratio between SUS and SUU is in order of increased preference at least 1:1.5, 1:2, 1:3.5, 1:5, 1:7.5, 1:10, 1:15.

20. The method as claimed in claim 18, wherein the oil source is sunflower seed, soybean, cottonseed, shea fruits, or rapeseed.

21. The method as claimed in claim 17, wherein the olein fraction is from high stearic high oleic (HSHO) sunflower oil.

22. The method as claimed in claim 17, wherein the olein fraction is from an oil selected from high stearic high oleic soybean oil, high stearic high oleic cottonseed oil and high stearic high oleic rapeseed (canola) oil.

23. The method as claimed in claim 17, wherein the olein fraction is from a tropical oil selected from shea olein and palm olein.

24. A method for increasing the stearin yield from a starting olein fraction upon fractionation of a starting oil, comprising the steps of:
   a) fractionating a starting oil having a ratio between SUS and SUU of at least 1:1.5 and a low SSS content, to obtain a stearin fraction and a starting olein fraction;
   b) performing the method as claimed in claim 1 on the starting olein fraction to obtain 1,3-selective intraesterified olein having a higher SUS content than the starting olein fraction; and
   c) fractionating the 1,3-selective intraesterified olein thus obtained to obtain a stearin fraction and an olein fraction.

25. The method as claimed in claim 24, wherein the total stearin yield from steps a) and c) together is higher than the stearin yield after fractionating the starting oil.

26. The method as claimed in claim 17, wherein the unsaturated U in SUS and/or SUU is oleic acid.

27. The method as claimed in claim 17, wherein the reaction time of the 1,3-selective enzymatic intraesterification is at least about 30 minutes.

28. The method as claimed in claim 17, wherein the 1,3-selective enzymatic intraesterification is performed by using lipase enzymes.

29. A composition comprising a 1,3-selective intraesterified olein, obtainable by performing a method as claimed in claim 17, wherein the 1,3-selective intraesterified olein is enriched in SUS as compared to the oil it was produced from.

30. A composition consisting of a stearin fraction, obtainable by performing the method as claimed in claim 24.

31. The composition of claim 30, wherein the composition is selected from the group consisting of a margarine, spreads, coatings, fillings, frying oils and cooking oils.

32. The method as claimed in claim 28, wherein the lipase enzyme comprises a lipase from *Rhizomucor miehei* (RMIM).

33. The method as claimed in claim 28, wherein the lipase enzyme comprises a lipase from *Thermomyces lanuginosis* (TLIM).

* * * * *